US011058321B2

(12) United States Patent
Hein (10) Patent No.: US 11,058,321 B2
(45) Date of Patent: Jul. 13, 2021

(54) CURRENT DRIVEN SENSOR FOR MAGNETIC NAVIGATION

(71) Applicant: Boston Scientific Scimed Inc., Maple Grove, MN (US)

(72) Inventor: Matthew Hein, Eden Prairie, MN (US)

(73) Assignee: Boston Scientific Scimed Inc., Maple Grove, MN (US)

( * ) Notice: Subject to any disclaimer, the term of this patent is extended or adjusted under 35 U.S.C. 154(b) by 753 days.

(21) Appl. No.: 15/847,076

(22) Filed: Dec. 19, 2017

(65) Prior Publication Data
US 2018/0168482 A1 Jun. 21, 2018

Related U.S. Application Data

(60) Provisional application No. 62/436,991, filed on Dec. 20, 2016.

(51) Int. Cl.
*A61B 5/00* (2006.01)
*A61B 5/06* (2006.01)
(Continued)

(52) U.S. Cl.
CPC .......... *A61B 5/062* (2013.01); *A61B 1/00147* (2013.01); *A61B 5/07* (2013.01);
(Continued)

(58) Field of Classification Search
CPC ....... A61B 5/062; A61B 5/07; A61B 1/00147; G01R 33/0017; G01R 33/0206; G01R 33/098
See application file for complete search history.

(56) References Cited

U.S. PATENT DOCUMENTS

| 5,631,557 A | 5/1997 | Davidson |
| 5,644,230 A | 7/1997 | Pant et al. |

(Continued)

FOREIGN PATENT DOCUMENTS

| EP | 0696357 B1 | 2/1996 |
| JP | 2003-502876 A | 1/2003 |

(Continued)

OTHER PUBLICATIONS

International Search Report and Written Opinion issued in PCT/US2017/067111, dated May 8, 2018, 19 pages.

(Continued)

*Primary Examiner* — Joanne M Hoffman
(74) *Attorney, Agent, or Firm* — Faegre Drinker Biddle & Reath LLP (57) ABSTRACT

A tracking system that includes a sensor and a current driver. The sensor includes a substrate and magnetic sensor components configured to sense one or more magnetic fields and provide signals corresponding to the one or more magnetic fields. The magnetic sensor components are on the substrate and the substrate includes one or more conductive paths connected to one or more of the magnetic sensor components and intersecting one or more footprints of the magnetic sensor components. The current driver is configured to provide a regulated current to the one or more conductive paths intersecting the one or more footprints of the magnetic sensor components.

18 Claims, 3 Drawing Sheets

(51) Int. Cl.
  *G01R 33/02*     (2006.01)
  *G01R 33/00*     (2006.01)
  *A61B 5/07*      (2006.01)
  *A61M 25/10*     (2013.01)
  *A61B 1/00*      (2006.01)
  *G01R 33/09*     (2006.01)
  *A61B 8/12*      (2006.01)
  *A61B 18/14*     (2006.01)
  *A61B 8/00*      (2006.01)
  *A61B 34/20*     (2016.01)
  *A61B 18/00*     (2006.01)
  *A61B 5/283*     (2021.01)

(52) U.S. Cl.
  CPC ....... *A61M 25/104* (2013.01); *G01R 33/0017* (2013.01); *G01R 33/0206* (2013.01); *G01R 33/098* (2013.01); *A61B 5/283* (2021.01); *A61B 5/6852* (2013.01); *A61B 8/12* (2013.01); *A61B 8/4254* (2013.01); *A61B 18/1492* (2013.01); *A61B 34/20* (2016.02); *A61B 2018/0022* (2013.01); *A61B 2018/00839* (2013.01); *A61B 2034/2051* (2016.02); *A61B 2562/0223* (2013.01)

(56) References Cited

U.S. PATENT DOCUMENTS

| | | | |
|---|---|---|---|
| 5,994,989 | A | 11/1999 | Rowe et al. |
| 6,169,254 | B1 * | 1/2001 | Pant ................... G01R 33/0206 174/254 |
| 6,183,889 | B1 | 2/2001 | Koshiba et al. |
| 6,184,680 | B1 | 2/2001 | Shinoura et al. |
| 6,273,322 | B1 | 8/2001 | Yamamoto et al. |
| 6,484,118 | B1 * | 11/2002 | Govari ................... A61B 5/06 702/150 |
| 6,501,678 | B1 | 12/2002 | Lenssen et al. |
| 6,536,123 | B2 | 3/2003 | Tamura |
| 6,593,884 | B1 * | 7/2003 | Gilboa ................... A61B 5/06 342/448 |
| 6,690,963 | B2 | 2/2004 | Ben-Haim et al. |
| 6,836,971 | B1 | 1/2005 | Wan |
| 7,298,140 | B2 | 11/2007 | Honkura et al. |
| 7,301,332 | B2 | 11/2007 | Govari et al. |
| 7,870,678 | B2 | 1/2011 | Kwon et al. |
| 8,390,279 | B2 | 3/2013 | Klocke et al. |
| 8,391,952 | B2 | 3/2013 | Anderson |
| 8,750,961 | B1 | 6/2014 | Ries et al. |
| 9,002,675 | B2 | 4/2015 | McIntyre et al. |
| 9,801,563 | B2 | 10/2017 | Bernstein |
| 10,782,114 | B2 | 9/2020 | Hein et al. |
| 2001/0026222 | A1 * | 10/2001 | Canady, Jr. ............ A61B 5/113 340/573.1 |
| 2002/0026197 | A1 | 2/2002 | Foley et al. |
| 2003/0123198 | A1 | 7/2003 | Sugawara et al. |
| 2003/0231098 | A1 | 12/2003 | Wan |
| 2004/0124835 | A1 | 7/2004 | Kimura |
| 2005/0270020 | A1 * | 12/2005 | Peczalski ............. G01R 33/093 324/247 |
| 2007/0080682 | A1 * | 4/2007 | Govari ............... G01R 33/0206 324/247 |
| 2007/0200564 | A1 | 8/2007 | Motz et al. |
| 2007/0260139 | A1 | 11/2007 | Minai et al. |
| 2008/0052931 | A1 | 3/2008 | Kwon et al. |
| 2008/0052932 | A1 | 3/2008 | Xue et al. |
| 2010/0171492 | A1 | 7/2010 | Klocke et al. |
| 2011/0234218 | A1 | 9/2011 | Lagouge |
| 2011/0248706 | A1 | 10/2011 | Davis et al. |
| 2012/0038357 | A1 | 2/2012 | Brandon et al. |
| 2012/0081111 | A1 | 4/2012 | Kim et al. |
| 2012/0153942 | A1 | 6/2012 | Van et al. |
| 2012/0299587 | A1 | 11/2012 | Rieger et al. |
| 2013/0127454 | A1 | 5/2013 | Ungaretti et al. |
| 2013/0169272 | A1 | 7/2013 | Eichler et al. |
| 2014/0276004 | A1 | 9/2014 | Strupeck et al. |
| 2014/0327437 | A1 | 11/2014 | Han et al. |
| 2015/0087921 | A1 | 3/2015 | Felix et al. |
| 2016/0135668 | A1 | 5/2016 | Gat et al. |
| 2016/0161531 | A1 * | 6/2016 | Avery ................... G01R 33/098 307/31 |
| 2016/0245877 | A1 | 8/2016 | Deak |
| 2017/0021172 | A1 | 1/2017 | Perez et al. |
| 2017/0059361 | A1 * | 3/2017 | Nagarkar ............ G01R 33/0052 |
| 2017/0325715 | A1 | 11/2017 | Mehendale et al. |
| 2018/0042518 | A1 | 2/2018 | Fruci et al. |
| 2018/0093042 | A1 | 4/2018 | Klemm et al. |
| 2018/0132360 | A1 | 5/2018 | Wang et al. |
| 2018/0153436 | A1 | 6/2018 | Olson |
| 2018/0172420 | A1 | 6/2018 | Hein et al. |
| 2018/0172865 | A1 | 6/2018 | Hein et al. |
| 2018/0220928 | A1 | 8/2018 | Blood et al. |
| 2018/0220929 | A1 | 8/2018 | Blood et al. |
| 2019/0025040 | A1 * | 1/2019 | Andreason ............. A61B 5/062 |

FOREIGN PATENT DOCUMENTS

| | | |
|---|---|---|
| JP | 2007-147593 A | 6/2007 |
| JP | 2012-523566 A | 10/2012 |
| WO | 1995009562 A1 | 4/1995 |
| WO | 2014207738 A1 | 12/2014 |
| WO | 2016087970 A1 | 6/2016 |
| WO | 2016196985 A1 | 12/2016 |

OTHER PUBLICATIONS

International Search Report and Written Opinion issued in PCT/US2018/016895, dated Apr. 13, 2018, 11 pages.

International Search Report and Written Opinion issued in PCT/US2018016876, dated Apr. 11, 2018, 10 pages.

PCT Invitation to Pay Additional Fees issued in PCT/US2017067111, dated Mar. 15, 2018, 16 pages.

\* cited by examiner

CURRENT DRIVEN SENSOR FOR MAGNETIC NAVIGATION

CROSS-REFERENCE TO RELATED APPLICATION

This application claims priority to Provisional Application No. 62/436,991, filed Dec. 20, 2016, which is herein incorporated by reference in its entirety.

TECHNICAL FIELD

The present disclosure relates to systems and methods for tracking devices. More specifically, the disclosure relates to systems and methods for electro-magnetically tracking medical devices used in medical procedures.

BACKGROUND

A variety of systems and methods can be used to track devices. One type of tracking system uses externally generated magnetic fields that are sensed by at least one tracking sensor in the tracked device. The externally generated magnetic fields provide a fixed frame of reference and the tracking sensor senses the magnetic fields to determine the location of the sensor in relation to the fixed frame of reference. Often, the tracking sensor is based on inductive coil technology. In these sensors, one to six or more inductive coils of near equal size and sensitivity may be used to make a 5 or 6 degree-of-freedom (DOF) magnetic field tracking sensor. The inductive coils in the tracking sensor sense the externally generated magnetic fields and each of the inductive coils provides a current based on the magnetic fields.

Often, medical devices to be tracked are very small. For example, probes, such as catheters, are inserted into a patient through the patient's vascular system and/or a catheter lumen. Each of the probes includes at least one magnetic field tracking sensor that senses magnetic fields to determine the location of the sensor in relation to the magnetic fields. As these probes become smaller and/or carry more components, the space or real estate available for the magnetic tracking sensor decreases, which results in the magnetic tracking sensor being made smaller. As a result, parasitic electro-magnetic effects become more and more relevant to accurately sensing the magnetic fields and the determination of the location of the tracking sensor.

SUMMARY

Example 1 is a tracking system including a sensor and a current driver. The sensor includes a substrate and magnetic sensor components configured to sense one or more magnetic fields and provide signals corresponding to the one or more magnetic fields. The magnetic sensor components are on the substrate and the substrate includes one or more conductive paths connected to one or more of the magnetic sensor components and intersecting one or more footprints of the magnetic sensor components. The current driver is configured to provide a regulated current to the one or more conductive paths intersecting the one or more footprints of the magnetic sensor components.

Example 2 is the tracking system of Example 1, wherein the sensor includes a package that houses the substrate and the magnetic sensor components and the package has a diameter of not more than 2 millimeters.

Example 3 is the tracking system of any one of Examples 1 and 2, wherein the sensor includes a package that houses the substrate and the magnetic sensor components and the package has a diameter in a range from 0.2 millimeters to 2 millimeters.

Example 4 is the tracking system of any one of Examples 1-3, wherein the regulated current provided by the current driver is a constant current.

Example 5 is the tracking system of any one of Examples 1-4, wherein the magnetic sensor components include one or more of a magneto-resistive magnetic sensor, a giant magneto-impedance magnetic sensor, and a flux-gate magnetic sensor.

Example 6 is the tracking system of any one of Examples 1-5, including a probe configured to be inserted into a patient, wherein the sensor is configured to be situated in the probe for tracking a location of the probe in the patient.

Example 7 is the tracking system of any one of Examples 1-6, including a control module configured to receive the signals and determine a location of the sensor and to compensate for an offset magnetic field generated by the regulated current provided to the one or more conductive paths intersecting the one or more footprints of the magnetic sensor components to determine the location of the sensor.

Example 8 is a tracking system including a probe, a tracking sensor, a control module, and a current driver. The probe is configured to be inserted into a patient. The tracking sensor is configured to be situated in the probe to track a location of the probe in the patient. The tracking sensor includes a housing, a substrate configured to be situated in the housing, and a plurality of magnetic sensor components on the substrate and configured to sense magnetic fields and provide signals corresponding to the magnetic fields. The substrate includes one or more conductive paths connected to one or more of the plurality of magnetic sensor components and intersecting one or more footprints of the plurality of magnetic sensor components. The control module is configured to receive the signals and determine the location of the probe in the patient. The current driver is configured to provide a regulated current to the one or more conductive paths intersecting the one or more footprints of the plurality of magnetic sensor components to sense the magnetic fields and reduce error in determining the location of the probe in the patient.

Example 9 is the tracking system of Example 8, wherein the housing has a diameter of not more than 2 millimeters.

Example 10 is the tracking system of any one of Examples 8 and 9, wherein the control module is configured to compensate for an offset magnetic field generated by the regulated current provided to the one or more conductive paths intersecting the one or more footprints of the plurality of magnetic sensor components to determine the location of the probe in the patient.

Example 11 is the tracking system of any one of Examples 8-10, including at least one other component on the substrate and the substrate includes at least one conductive path connected to the at least one other component and intersecting at least one footprint of the plurality of magnetic sensor components, wherein the current driver is configured to provide other regulated current to the other component via the at least one conductive path.

Example 12 is a method of tracking. The method includes: sensing one or more magnetic fields via magnetic sensor components on a substrate including one or more conductive paths connected to one or more of the magnetic sensor components and intersecting one or more footprints of the magnetic sensor components; providing signals corresponding to the one or more magnetic fields sensed by the magnetic sensor components; and providing a regulated current to the one or more conductive paths intersecting the one or more footprints of the magnetic sensor components to sense the one or more magnetic fields.

Example 13 is the method of Example 12, wherein providing the regulated current includes providing a constant current.

Example 14 is the method of any of Examples 12 and 13, including receiving the signals at a control module and determining a location of the magnetic sensor components by compensating for an offset magnetic field generated by the regulated current provided to the one or more conductive paths intersecting the one or more footprints of the magnetic sensor components.

Example 15 is the method of any of Examples 12-14, wherein the substrate and the magnetic sensor components are housed in a housing having a diameter of not more than 2 millimeters and the housing is configured to be inserted into a probe that is configured to be inserted into a patient for tracking a location of the probe in the patient.

Example 16 is a tracking system including a sensor and a current driver. The sensor is configured to sense one or more magnetic fields and includes a substrate and magnetic sensor components configured to sense the one or more magnetic fields and provide signals corresponding to the one or more magnetic fields. The magnetic sensor components are on the substrate and the substrate includes one or more conductive paths connected to one or more of the magnetic sensor components and intersecting one or more footprints of the magnetic sensor components. The current driver is configured to provide a regulated current to the one or more conductive paths intersecting the one or more footprints of the magnetic sensor components.

Example 17 is the tracking system of Example 16, wherein the sensor includes a package that houses the substrate and the magnetic sensor components.

Example 18 is the tracking system of Example 17, wherein the package has a diameter of not more than 2 millimeters.

Example 19 is the tracking system of Example 17, wherein the package has a diameter in a range from 0.2 millimeters to 2 millimeters.

Example 20 is the tracking system of Example 16, wherein the regulated current provided by the current driver is a constant current.

Example 21 is the tracking system of Example 16, wherein the sensor includes three magnetic sensor components for sensing up to six degrees of freedom.

Example 22 is the tracking system of Example 16, wherein the magnetic sensor components include one or more of a magneto-resistive magnetic sensor, a giant magneto-impedance magnetic sensor, and a flux-gate magnetic sensor.

Example 23 is the tracking system of Example 16, including a probe configured to be inserted into a patient, wherein the sensor is configured to be situated in the probe for tracking a location of the probe in the patient.

Example 24 is the tracking system of Example 16, including a control module configured to receive the signals and determine a location of the sensor and to compensate for an offset magnetic field generated by the regulated current provided to the one or more conductive paths intersecting the one or more footprints of the magnetic sensor components to determine the location of the sensor.

Example 25 is the tracking system of Example 24, wherein the signals are received wirelessly from the sensor.

Example 26 is a tracking system including a probe, a tracking sensor, a control module, and a current driver. The probe is configured to be inserted into a patient. The tracking sensor is configured to be situated in the probe to track a location of the probe in the patient based on generated magnetic fields. The tracking sensor includes a housing, a substrate configured to be situated in the housing, and a plurality of magnetic sensor components on the substrate and configured to sense the generated magnetic fields and provide signals corresponding to the generated magnetic fields. The substrate includes one or more conductive paths connected to one or more of the plurality of magnetic sensor components and intersecting one or more footprints of the plurality of magnetic sensor components. The control module is configured to receive the signals and determine the location of the probe in the patient. The current driver is configured to provide a regulated current to the one or more conductive paths intersecting the one or more footprints of the plurality of magnetic sensor components to reduce error in the location of the probe in the patient.

Example 27 is the tracking system of Example 26, wherein the housing has a diameter of not more than 2 millimeters.

Example 28 is the tracking system of Example 26, wherein the housing has a diameter in a range from 0.2 millimeters to 2 millimeters.

Example 29 is the tracking system of Example 26, wherein the probe is one of a catheter, a treatment catheter, a balloon angioplasty catheter, an ablation catheter, a mapping catheter, an imaging probe, an ultra-sound imaging probe, and a diagnostic probe.

Example 30 is the tracking system of Example 26, including at least one other component on the substrate and the substrate includes at least one conductive path connected to the at least one other component and intersecting at least one footprint of the plurality of magnetic sensor components, wherein the current driver is configured to provide regulated current to the other component via the at least one conductive path.

Example 31 is a method of tracking. The method includes: sensing one or more magnetic fields via magnetic sensor components on a substrate including one or more conductive paths connected to one or more of the magnetic sensor components and intersecting one or more footprints of the magnetic sensor components; providing signals corresponding to the one or more magnetic fields sensed by the magnetic sensor components; and providing a regulated current to the one or more conductive paths intersecting the one or more footprints of the magnetic sensor components.

Example 32 is the method of Example 31, wherein providing the regulated current includes providing a constant current.

Example 33 is the method of Example 31, including receiving the signals at a control module and determining a location of the magnetic sensor components by compensating for an offset magnetic field generated by the regulated current provided to the one or more conductive paths intersecting the one or more footprints of the magnetic sensor components.

Example 34 is the method of Example 31, wherein the substrate and the magnetic sensor components are housed in a housing having a diameter of not more than 2 millimeters.

Example 35 is the method of Example 34, wherein the housing is configured to be inserted into a probe that is configured to be inserted into a patient for tracking a location of the probe in the patient.

While multiple embodiments are disclosed, still other embodiments of the present disclosure will become apparent to those skilled in the art from the following detailed description, which shows and describes illustrative embodiments of the disclosure. Accordingly, the drawings and detailed description are to be regarded as illustrative in nature and not restrictive.

While the disclosure is amenable to various modifications and alternative forms, specific embodiments have been shown by way of example in the drawings and are described in detail below. The intention, however, is not to limit the disclosure to the particular embodiments described. On the contrary, the disclosure is intended to cover all modifications, equivalents, and alternatives falling within the scope of the disclosure as defined by the appended claims.

DETAILED DESCRIPTION

The space or real estate available for a magnetic tracking sensor decreases as probes become smaller and/or carry more components. This results in decreasing the size of the magnetic tracking sensor. To make a smaller magnetic tracking sensor, non-passive magnetic sensor components, such as magneto-resistive (MR) sensor components, giant magneto-impedance (GMI) sensor components, and/or fluxgate sensor components, can be used in the tracking sensor to sense the magnetic fields. MR sensor components include anisotropic magneto-resistive (AMR) sensor components, giant magneto-resistive (GMR) sensor components, tunneling magneto-resistive (TMR) sensor components, Hall effect sensor components, colossal magneto-resistive (CMR) sensor components, extraordinary magneto-resistive (EMR) sensor components, and spin Hall sensor components. The smaller tracking sensors can be configured to sense up to at least 6 DOF.

The non-passive magnetic sensor components used in the smaller tracking sensors are powered by voltages or currents to drive or excite the components. Due to space or real estate constraints, conductive traces for driving the magnetic sensor components and for conveying a sensed value for one or more of the magnetic sensor components pass underneath at least one of the other magnetic sensor components. If the magnetic sensor components are driven by a constant voltage, a change in resistance due to the applied magnetic fields results in a change in current through the component. This generates a new parasitic magnetic field, which the other magnetic sensor components may sense. The new parasitic magnetic fields can be very difficult to compensate for and they may cause errors or inaccuracies in the determination of the location of the tracking sensor. In the present disclosure, the magnetic sensor components are driven by a regulated current, such as a constant current. Changes in the resistance of a magnetic sensor component due to the applied magnetic fields results in a change in the voltage across the magnetic sensor component, which does not generate a new parasitic magnetic field. As a result, it is much easier to determine an accurate location of the tracking sensor.

Figure 1:
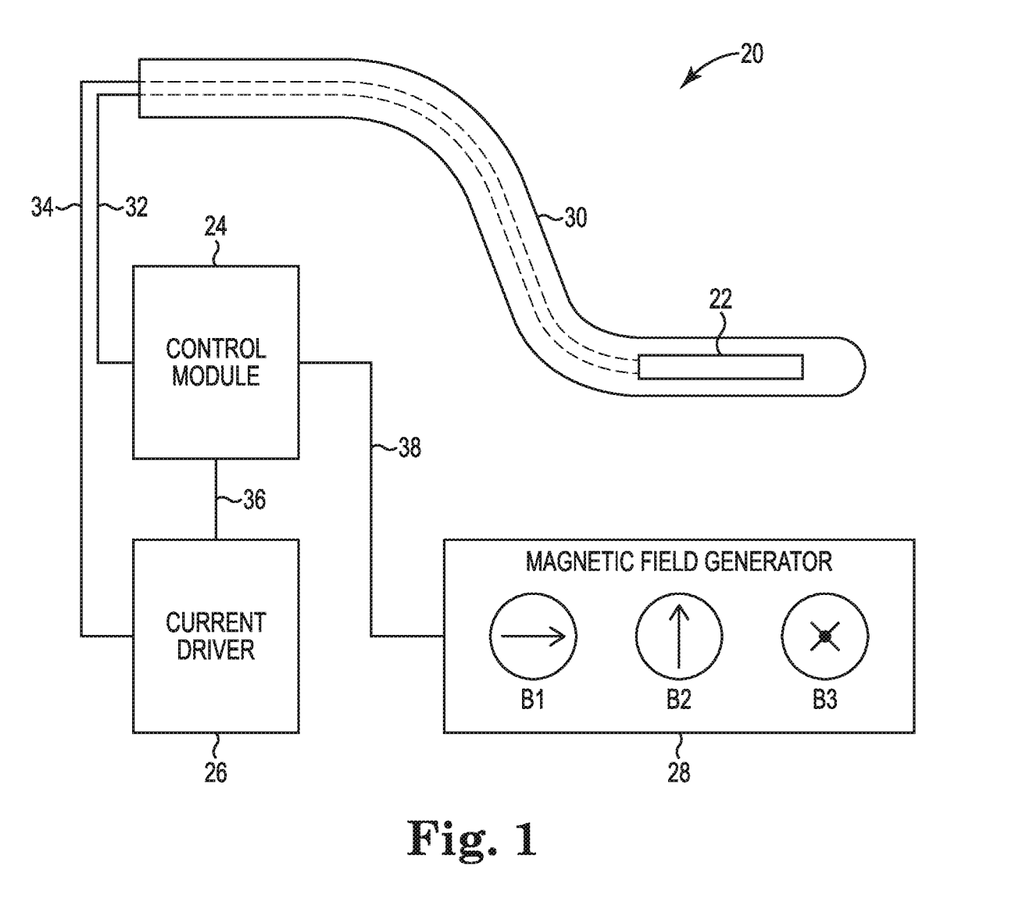
FIG. 1 is a diagram illustrating a tracking system, according to embodiments of the disclosure.

FIG. 1 is a diagram illustrating a tracking system 20, according to embodiments of the disclosure. The tracking system 20 includes a tracking device or sensor 22, a control module 24, a current driver 26, and a magnetic field generator 28. The tracking sensor 22 can be fixed to a single location in a probe 30, such as close to the distal end or tip of the probe 30. In other embodiments, the tracking sensor 22 can be fixed to another suitable device.

The tracking system 20 magnetically tracks the tracking sensor 22 and provides the location of the tracking sensor 22 and the probe 30 in relation to magnetic fields generated by the magnetic field generator 28. The magnetic fields generated by the magnetic field generator 30 provide a frame of reference for the tracking system 20. In some embodiments, the magnetic field generator 28 generates the magnetic fields to provide a fixed frame of reference for the tracking system 20, where the tracking sensor 22 senses the magnetic fields to determine the location of the tracking sensor 22 in relation to the fixed frame of reference.

In some embodiments, the tracking system 20 can be used in a medical procedure, where the probe 30 is configured to be inserted into a patient and the tracking sensor 22 is configured for tracking a location of the probe 30 in the patient. In some embodiments, the probe 30 is one of a catheter, a treatment catheter, a balloon angioplasty catheter, an ablation catheter, a mapping catheter, an imaging probe, an ultra-sound imaging probe, and a diagnostic probe. In other embodiments, the tracking sensor 22 can be fixed in another suitable device for another suitable purpose.

The tracking sensor 22 is communicatively connected to the control module 24 by communications path 32 and to the current driver 26 by communications path 34. The control module 24 is communicatively coupled to the current driver 26 by communications path 36 and to the magnetic field generator 28 by communications path 38. In some embodiments, the tracking sensor 22 is communicatively coupled to the control module 24 and to the current driver 26 by the same communications path, such as communications path 32. In these embodiments, the current driver 26 provides regulated current to the tracking sensor 22 via the communications path and the control module 24 receives sensed signals from the tracking sensor 22 via the same communications path.

The magnetic field generator 28 is configured to provide one or more magnetic fields. For example, the magnetic field generator 28 is configured to generate three magnetic fields B1, B2, and B3. Each of the magnetic fields B1, B2, and B3 is directed in a different direction, as indicated by arrows in FIG. 1. Magnetic field B1 is a magnetic field in the horizontal direction, magnetic field B2 is a magnetic field in the vertical direction, and magnetic field B3 is a magnetic field into the page of FIG. 1. The control module 24 is configured to control the magnetic field generator 28 via communications path 38 to generate one or more of the magnetic fields B1, B2, and B3 for tracking the tracking sensor 22.

The tracking sensor 22 is configured to sense each of the magnetic fields B1, B2, and B3 and provide signals to the control module 24 that correspond to each of the sensed magnetic fields B1, B2, and B3. The tracking sensor 22 is configured to sense up to at least 6 DOF of the tracking sensor 22 and probe 30. The control module 24 receives the signals from the tracking sensor 22 via communications path 32 and determines the position and location of the tracking sensor 22 and probe 30 in relation to the generated magnetic fields B1, B2, and B3.

The tracking sensor 22 includes magnetic sensor elements or components that sense one or more of the magnetic fields generated by the magnetic field generator 28 and provide signals corresponding to the sensed magnetic fields. The tracking sensor 22 includes non-passive magnetic sensor components activated by a current source, and the tracking sensor 22 can be configured to sense up to at least 6 DOF. In some embodiments, the tracking sensor 22 includes non-passive components, such as MR sensor components, GMI sensor components, and/or flux-gate sensor components. In some embodiments, the tracking sensor 22 includes MR sensor components, such as one or more of AMR sensor components, GMR sensor components, TMR sensor components, Hall effect sensor components, CMR sensor components, EMR sensor components, and spin Hall sensor components.

The current driver 26 is configured to provide a regulated current to each of the magnetic sensor components in the tracking sensor 22 via communications path 34. The control module 24 controls the current driver 26 to provide the regulated current to the tracking sensor 22. In some embodiments, the regulated current is a constant current provided to each of the magnetic sensor components in the tracking sensor 22.

The magnetic sensor components in the tracking sensor 22 receive the regulated current and in response to one or more of the applied magnetic fields each of the magnetic sensor components provide sensed signals to the control module 24. Each of the magnetic sensor components has a magnetic sensor footprint on a substrate in the tracking sensor 22. The magnetic sensor footprint is the size of the magnetic sensor component and each of the magnetic sensor components is placed in its footprint on the substrate in the tracking sensor 22.

Due to space or real estate constraints in the tracking sensor 22, at least some of the conductive traces for driving the magnetic sensor components and conveying sensed signals for one or more of the magnetic sensor components pass underneath or through the footprint of at least one of the other magnetic sensor components in the tracking sensor 22. Since the magnetic sensor components are driven by a regulated current, such as a constant current, the changes in the resistance of a magnetic sensor component due to the applied magnetic fields result in changes in the voltage across the magnetic sensor component, which does not generate a new parasitic magnetic field, which would otherwise adversely affect the determination of the location of the tracking sensor 22 by the control module 24. In some embodiments, the tracking sensor 22 includes a controller or processor configured to receive signals from the magnetic sensor components and transmit signals wirelessly to the control module 24 via communications path 32.

The control module 24 is configured to control the current driver 26 to provide the regulated current to the tracking sensor 22 and to control the magnetic field generator 28 to generate one or more of the magnetic fields B1, B2, and B3 for tracking the tracking sensor 22. The control module 24 receives the signals from the tracking sensor 22 and determines the position and location of the tracking sensor 22 and probe 30 in relation to the magnetic fields B1, B2, and B3. The control module 24 compensates for offset magnetic fields generated by the regulated current provided to the magnetic sensor components via one or more conductive paths intersecting the one or more footprints of magnetic sensor components to determine the location of the tracking sensor 22.

Figure 2:
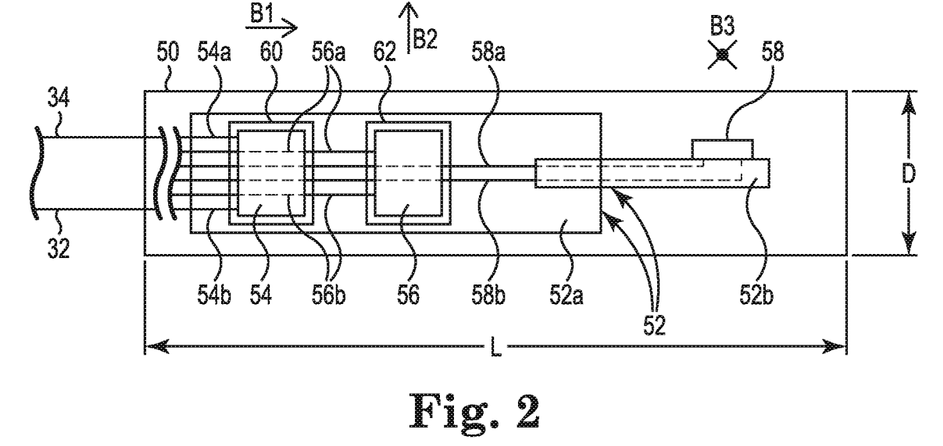
FIG. 2 is a diagram illustrating a cutaway, top view of a tracking sensor, according to embodiments of the disclosure.
Figure 3:
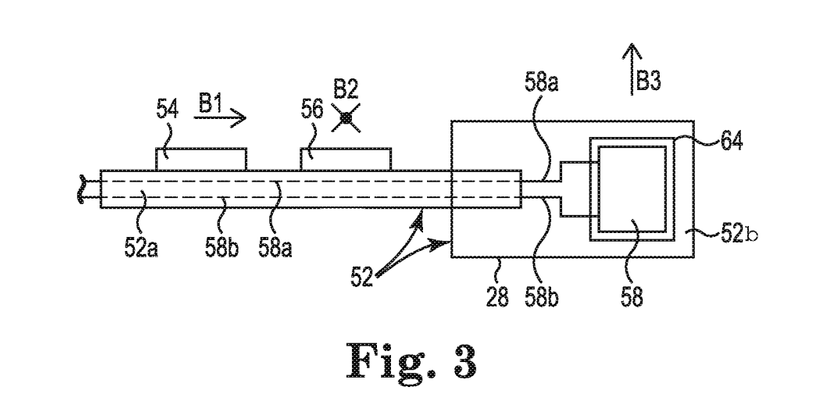
FIG. 3 is a diagram illustrating a side view of the substrate and the three magnetic sensor components of FIG. 2, according to embodiments of the disclosure.

FIG. 2 is a diagram illustrating a cutaway, top view of tracking sensor 22, according to embodiments of the disclosure. The tracking sensor 22 includes a package or housing 50, a substrate 52, and three magnetic sensor components 54, 56, and 58. FIG. 3 is a diagram illustrating a side view of the substrate 52 and the three magnetic sensor components 54, 56, and 58 of FIG. 2, according to embodiments of the disclosure.

The tracking sensor 22 is configured to sense magnetic fields B1, B2, and B3. Also, the tracking sensor 22 is configured to provide signals corresponding to the sensed magnetic fields B1, B2, and B3. The tracking sensor 22 receives regulated current, such as constant current, from the current driver 26 via communications path 34. The control module 24 receives the signals corresponding to the sensed magnetic fields B1, B2, and B3 from the tracking sensor 22 via communications path 32. In some embodiments, the tracking sensor 22 receives the regulated current from the current driver 26 and communicates the signals to the control module 24 via the same communications path. In some embodiments, communications path 32 includes multiple conductive paths or traces. In some embodiments, communications path 34 includes multiple conductive paths or traces.

The three magnetic sensor components 54, 56, and 58 are secured on the substrate 52 and the substrate 52 is secured in the housing 50. The housing 50 houses the substrate 52 and the magnetic sensor components 54, 56, and 58. In some embodiments, the tracking sensor 22 includes fewer than three magnetic sensor components. In some embodiments, the tracking sensor 22 includes more than three magnetic sensor components.

The package or housing 50 surrounds the substrate 52 and the magnetic sensor components 54, 56, and 58 on all sides. The housing 50 is cylindrically shaped having a length L and a diameter D. In some embodiments, the housing 50 has a length L that is less than 5 millimeters (mm). In some embodiments, the housing 50 has a length L that is less than 3 mm. In some embodiments, the housing 50 has a length L that is less than 2 mm. In some embodiments, the housing 50 has a diameter D that is less than (no more than) 2 mm. In some embodiments, the housing 50 has a diameter D that is between 0.2 mm and 2.0 mm. In some embodiments, the housing 50 has a different shape, such as a three-dimensional rectangular or cuboid shape.

The three magnetic sensor components 54, 56, and 58 are mounted on the substrate 52 in three component footprints 60, 62, and 64, respectively, on the substrate 52. The substrate 52 includes a first substrate portion 52a and a second substrate portion 52b. The magnetic sensor components 54 and 56 are mounted in the component footprints 60 and 62, respectively, on the first substrate portion 52a, and the magnetic sensor component 58 is mounted in the component footprint 64 on the second substrate portion 52b. The first substrate portion 52a and the second substrate portion 52b are not coplanar. In some embodiments, the first substrate portion 52a and the second substrate portion 52b are perpendicular to one another. In some embodiments, the first substrate portion 52a and the second substrate portion 52b are separate pieces of material connected together, such as by soldering. In some embodiments, the substrate 52 is a flex circuit that is twisted to form the non-coplanar first and second substrate portions 52a and 52b. In some embodiments, the substrate 52 is printed circuit board material.

The magnetic sensor components 54, 56, and 58 are electrically coupled to the control module 24 and the current driver 26 through conductive paths or traces on the substrate 52. These conductive paths are connected to one or more of the communication paths 32 and 34. Each of the magnetic sensor components 54, 56, and 58 receives a regulated current, such as a constant current, from the current driver 26 through the conductive paths. Also, each of the magnetic sensor components 54, 56, and 58 provides signals corresponding to sensed magnetic fields to the control module 24 through the conductive paths. In FIGS. 2 and 3, two conductive paths are illustrated as being connected to each of the three magnetic sensor components 54, 56, and 58. In other illustrations and embodiments, more than two conductive paths can be connected to each of the magnetic sensor components 54, 56, and 58.

The magnetic sensor components 54, 56, and 58 are electrically coupled to different conductive paths. The magnetic sensor component 54 is electrically coupled to conductive paths 54a and 54b, which are electrically coupled to one or more of the communications paths 32 and 34. The magnetic sensor component 56 is electrically coupled to conductive paths 56a and 56b, which are electrically coupled to one or more of the communications paths 32 and 34, where each of the conductive paths 56a and 56b passes under magnetic sensor component 54 and through, intersecting footprint 60. The magnetic sensor component 58 is electrically coupled to conductive paths 58a and 58b, which are electrically coupled to one or more of the communications paths 32 and 34, where each of the conductive paths 58a and 58b passes under magnetic sensor components 54 and 56 and through, intersecting each of the footprints 60 and 62.

The magnetic sensor components 54, 56, and 58 are configured to sense one or more of the magnetic fields B1, B2, and B3 and provide signals corresponding to the sensed one or more magnetic fields. The magnetic sensor component 54 is configured to primarily sense magnetic field B1, the magnetic sensor component 56 is configured to primarily sense magnetic field B2, and the magnetic sensor component 58 is configured to primarily sense magnetic field B3. The three magnetic sensor components 54, 56, and 58 can sense up to at least six DOF. In some embodiments, each of the magnetic sensor components 54, 56, and 58 is configured to primarily sense a different on of the magnetic fields B1, B2, and B3. In some embodiments, each of the magnetic sensor components 54, 56, and 58 is configured to sense more than one of the magnetic fields B1, B2, and B3.

In some embodiments, the magnetic sensor components 54, 56, and 58 include one or more MR sensor components, GMI sensor components, and/or flux-gate sensor components. In some embodiments, the magnetic sensor components 54, 56, and 58 include one or more MR sensor components, such as one or more AMR sensor components, GMR sensor components, TMR sensor components, Hall effect sensor components, CMR sensor components, EMR sensor components, and spin Hall sensor components.

The control module 24 receives the signals corresponding to the sensed magnetic fields and determines a location of the tracking sensor 22. The control module also compensates for an offset magnetic field generated by the regulated current provided to the one or more conductive paths intersecting the one or more footprints 60, 62, and 64 of the magnetic sensor components 54, 56, and 58 to determine the location of the sensor.

In some embodiments, the tracking sensor 22 includes at least one other component (not shown for clarity) that is electrically coupled to at least one other conductive path on the substrate 52. This at least one other conductive path intersects at least one footprint of the footprints 60, 62, and 64. In these embodiments, current driver 24 can provide another regulated current to the other component via the at least one other conductive path, and control module 24 can compensate for another offset magnetic field in determining the location of the tracking sensor 22.

Figure 4:
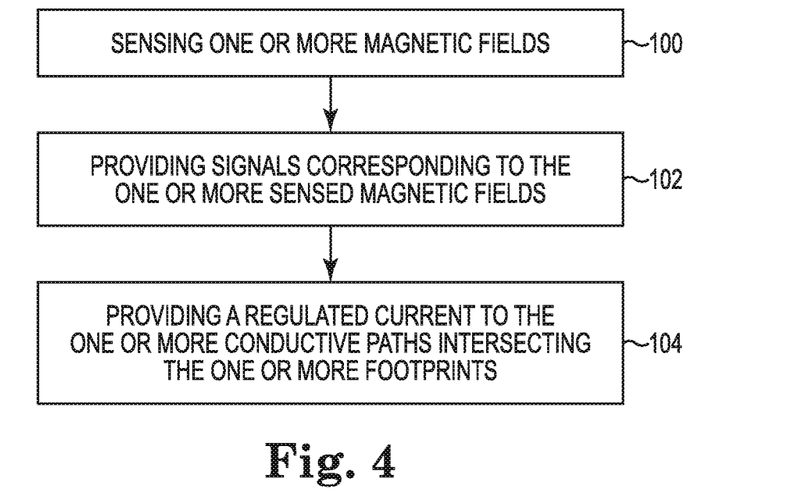
FIG. 4 is a diagram illustrating a method of tracking, according to embodiments of the disclosure.

FIG. 4 is a diagram illustrating a method of tracking, according to embodiments of the disclosure. At 100, the method includes sensing one or more magnetic fields via magnetic sensor components on a substrate including one or more conductive paths connected to one or more of the magnetic sensor components and intersecting one or more footprints of the magnetic sensor components. In some embodiments, the one or more magnetic fields include one or more of the three magnetic fields B1, B2, and B3. In some embodiments, the magnetic sensor components include one or more of the three magnetic sensor components 54, 56, and 58 and the substrate includes the substrate 52. In some embodiments, the conductive paths include one or more of the conductive paths 54a, 54b, 56a, 56b, 58a, and 58b and the footprints include one or more of the footprints 60, 62, and 64.

The method, at 102, includes providing signals corresponding to the one or more magnetic fields sensed by the magnetic sensor components. At 104, the method includes providing a regulated current to the one or more conductive paths intersecting the one or more footprints of the magnetic sensor components to sense the one or more magnetic fields. In some embodiments, providing the regulated current includes providing a constant current.

Further method steps include receiving the signals at a control module and determining a location of the magnetic sensor components, and compensating for an offset magnetic field generated by the regulated current provided to the one or more conductive paths intersecting the one or more footprints of the magnetic sensor components.

In some embodiments, the substrate and the magnetic sensor components are housed in a housing having a diameter of not more than 2 millimeters and the housing is configured to be inserted into a probe that is configured to be inserted into a patient for tracking a location of the probe in the patient.

Various modifications and additions can be made to the exemplary embodiments discussed without departing from the scope of the present disclosure. For example, while the embodiments described above refer to particular features, the scope of this disclosure also includes embodiments having different combinations of features and embodiments that do not include all of the described features. Accordingly, the scope of the present disclosure is intended to embrace all such alternatives, modifications, and variations as fall within the scope of the claims, together with all equivalents thereof.

I claim:
1. A tracking system, comprising:
a sensor configured to sense one or more magnetic fields, wherein the sensor is configured for tracking a location within a patient, the sensor including:
a substrate; and
magnetic sensor components including magneto-resistive magnetic sensors configured to sense the one or more magnetic fields and provide voltage signals corresponding to the one or more magnetic fields, wherein the magnetic sensor components are on the substrate and the substrate includes one or more conductive paths connected to one or more of the magnetic sensor components and intersecting one or more footprints of the magnetic sensor components;

a current driver configured to provide a regulated current to each of the one or more conductive paths intersecting the one or more footprints of the magnetic sensor components, wherein the regulated current provided to each of the one or more conductive paths intersecting the one or more footprints of the magnetic sensor components generates one or more offset magnetic fields and one or more of the magneto-resistive magnetic sensors receives the regulated current through the one or more conductive paths, such that the regulated current passes through the one or more of the magneto-resistive magnetic sensors to provide the voltage signals that change based on the one or more magnetic fields; and a control module configured to receive the voltage signals and compensate for the one or more offset magnetic fields generated by the regulated current provided to the one or more conductive paths intersecting the one or more footprints of the magnetic sensor components to determine the location of the sensor.

2. The tracking system of claim 1, wherein the sensor includes a package that houses the substrate and the magnetic sensor components.

3. The tracking system of claim 2, wherein the package has a diameter of not more than 2 millimeters.

4. The tracking system of claim 2, wherein the package has a diameter in a range from 0.2 millimeters to 2 millimeters.

5. The tracking system of claim 1, wherein the regulated current provided by the current driver is a constant current.

6. The tracking system of claim 1, wherein the sensor includes three magnetic sensor components for sensing up to six degrees of freedom.

7. The tracking system of claim 1, wherein the magneto-resistive magnetic sensors include one or more giant magneto-impedance magnetic sensors.

8. The tracking system of claim 1, comprising:
a probe configured to be inserted into the patient, wherein the sensor is configured to be situated in the probe for tracking the location of the probe in the patient.

9. The tracking system of claim 1, wherein the voltage signals are received wirelessly from the sensor.

10. A tracking system, comprising:
a probe configured to be inserted into a patient;
a tracking sensor configured to be situated in the probe to track a location of the probe in the patient based on generated magnetic fields, the tracking sensor including:
a housing;
a substrate configured to be situated in the housing; and
a plurality of magnetic sensor components including magneto-resistive magnetic sensors on the substrate and configured to sense the generated magnetic fields and provide voltage signals corresponding to the generated magnetic fields, wherein the substrate includes one or more conductive paths connected to one or more of the plurality of magnetic sensor components and intersecting one or more footprints of the plurality of magnetic sensor components;
a control module configured to receive the signals and determine the location of the probe in the patient; and
a current driver configured to provide a regulated current to each of the one or more conductive paths intersecting the one or more footprints of the plurality of magnetic sensor components to reduce error in the location of the probe in the patient, wherein the regulated current generates one or more offset magnetic fields and the control module is configured to compensate for the one or more offset magnetic fields generated by the regulated current to determine the location of the probe in the patient, and wherein one or more of the magneto-resistive magnetic sensors receives the regulated current through the one or more conductive paths, such that the regulated current passes through the one or more of the magneto-resistive magnetic sensors to provide the voltage signals that change based on the one or more magnetic fields.

11. The tracking system of claim 10, wherein the housing has a diameter of not more than 2 millimeters.

12. The tracking system of claim 10, wherein the housing has a diameter in a range from 0.2 millimeters to 2 millimeters.

13. The tracking system of claim 10, wherein the probe is one of a catheter, a treatment catheter, a balloon angioplasty catheter, an ablation catheter, a mapping catheter, an imaging probe, an ultra-sound imaging probe, and a diagnostic probe.

14. The tracking system of claim 10, comprising at least one other component on the substrate and the substrate includes at least one conductive path connected to the at least one other component and intersecting at least one footprint of the plurality of magnetic sensor components, wherein the current driver is configured to provide regulated current to the other component via the at least one conductive path.

15. A method of tracking a magnetic sensor within a patient, comprising:
sensing one or more magnetic fields via magnetic sensor components including magneto-resistive magnetic sensors on a substrate including one or more conductive paths connected to one or more of the magnetic sensor components and intersecting one or more footprints of the magnetic sensor components;
providing voltage signals corresponding to the one or more magnetic fields sensed by the magneto-resistive magnetic sensors;
providing a regulated current to each of the one or more conductive paths intersecting the one or more footprints of the magnetic sensor components,
wherein the regulated current provided to each of the one or more conductive paths intersecting the one or more footprints of the magnetic sensor components generates one or more offset magnetic fields and one or more of the magneto-resistive magnetic sensors receives the regulated current through the one or more conductive paths, such that the regulated current passes through the one or more of the magneto-resistive magnetic sensors to provide the voltage signals that change based on the one or more magnetic fields;
receiving the voltage signals at a control module; and
determining, by the control module, a location of the magnetic sensor components by compensating for the offset magnetic field generated by the regulated current provided to the one or more conductive paths intersecting the one or more footprints of the magnetic sensor components.

16. The method of claim 15, wherein providing the regulated current includes providing a constant current.

17. The method of claim 15, wherein the substrate and the magnetic sensor components are housed in a housing having a diameter of not more than 2 millimeters.

18. The method of claim 17, wherein the housing is configured to be inserted into a probe that is configured to be inserted into the patient for tracking a location of the probe in the patient.

* * * * *